United States Patent [19]

Armstrong

[11] 4,215,476

[45] Aug. 5, 1980

[54] HEALTH SERVICES COMBINATION IRRIGATOR AND ASPIRATOR

[76] Inventor: Alexander S. Armstrong, 5679 Monroe St., Sylvania, Ohio 43560

[21] Appl. No.: 781,212

[22] Filed: Mar. 25, 1977

[51] Int. Cl.² ...................... A61C 17/04; A61M 1/00
[52] U.S. Cl. ...................... 433/80; 128/276; 128/240; 222/144.5; 128/225; 433/95
[58] Field of Search .......................... 32/40 R, 57, 33; 128/276, 277, 278, 225, 227, 229, 230, 214 F, 231, 232, 234, 235, 240, 241, DIG. 24, 305; 222/94, 95, 144.5

[56] References Cited

U.S. PATENT DOCUMENTS

| | | | |
|---|---|---|---|
| 605,178 | 6/1898 | Ferguson | 128/227 |
| 1,465,620 | 8/1923 | Anderson | 222/94 |
| 2,022,742 | 12/1935 | Salerni | 128/227 |
| 2,384,458 | 9/1945 | Dubay | 15/321 |
| 2,733,713 | 2/1956 | Kabnick | 128/230 |
| 3,074,451 | 1/1963 | Whitney | 128/DIG. 24 |
| 3,090,968 | 5/1963 | Buono | 128/DIG. 24 |
| 3,164,153 | 1/1965 | Zorzi | 128/224 |
| 3,208,145 | 9/1965 | Turner | 32/33 |
| 3,502,072 | 3/1970 | Stillman | 128/229 |
| 3,507,278 | 4/1970 | Werding | 128/225 |
| 3,624,907 | 12/1971 | Brass et al. | 32/40 R |
| 3,640,276 | 2/1972 | Dancy, Jr. | 128/214 F |
| 3,693,613 | 9/1972 | Kelman | 128/278 |
| 3,735,751 | 5/1973 | Katz | 128/276 |
| 3,749,090 | 7/1973 | Stewart | 128/276 |
| 3,830,405 | 8/1974 | Jaeger | 222/144.5 |
| 3,920,014 | 11/1975 | Banko | 128/276 |
| 3,993,218 | 11/1976 | Reichenberger | 222/144.5 |

FOREIGN PATENT DOCUMENTS 1418581  10/1965  France ........................... 222/94

Primary Examiner—Robert W. Michell
Assistant Examiner—Arthur S. Rose
Attorney, Agent, or Firm—Wilson, Fraser, Barker & Clemens

[57] ABSTRACT

A health services combination irrigation and aspiration device adapted to serve more than one irrigation function and to require the use of only one hand by the operator. The instrument includes a handpiece, a supply station and a control for the regulation and selection among fluid and vacuum means. While the instrument is well adapted to dental work, particularly root canal methodology, it also supplies a need for a general purpose medical instrument which can provide suction and lavage of a tissue or organ surface with one or more of selected medicinal solutions, including distilled water or saline solution. Notably, the handpiece tip system is small enough to allow easy access to remote tissue surfaces while the angled design allows access to difficult to reach interior surfaces.

7 Claims, 12 Drawing Figures

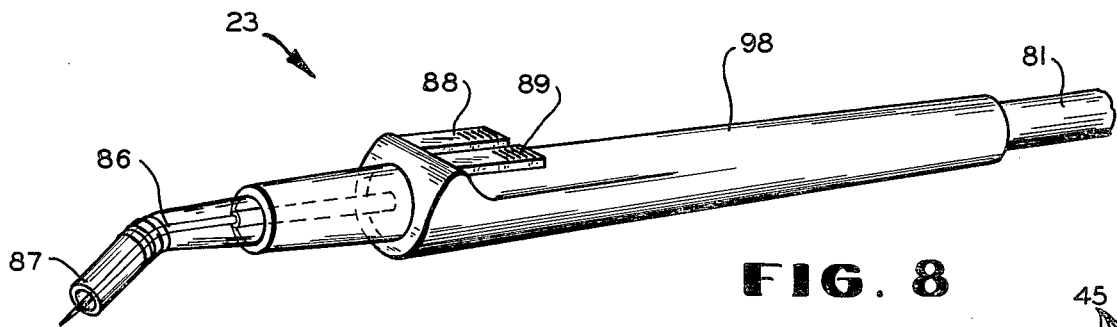
FIG. 8
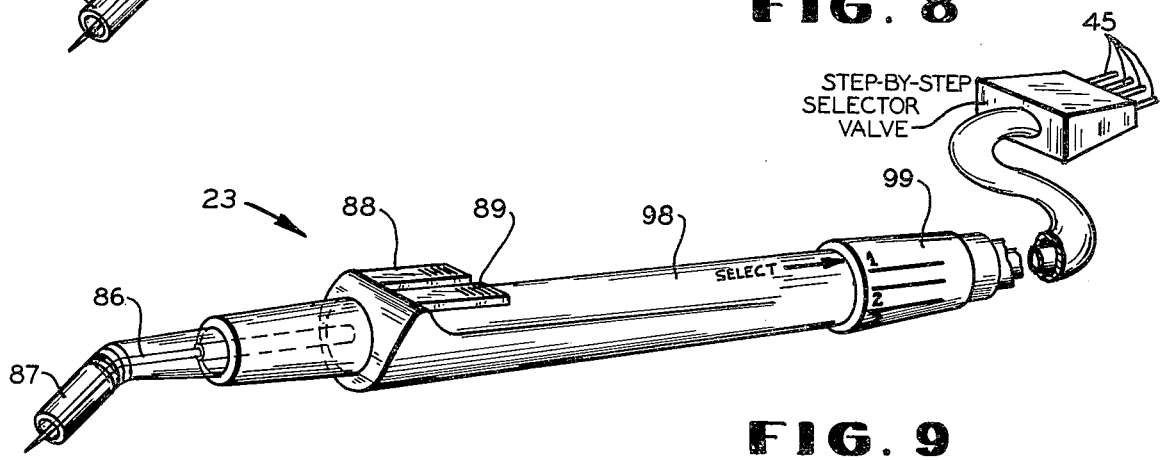
FIG. 9
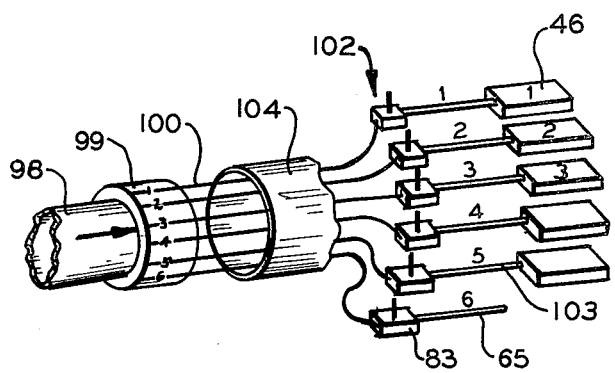
FIG. 10
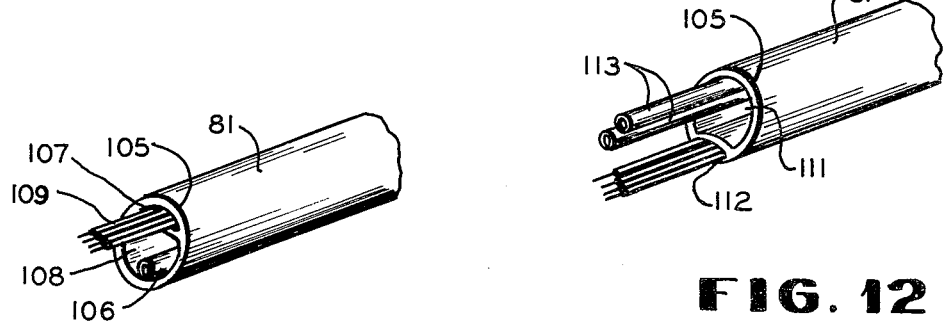
FIG. 11
FIG. 12

HEALTH SERVICES COMBINATION IRRIGATOR AND ASPIRATOR

BACKGROUND OF THE INVENTION

The invention relates to apparatus for medical/surgical/dental procedures which require the use of medicinal fluids and suction in patient treatment. In particular the invention relates to a system capable of storing and dispensing fluids under controlable pressures while at the same time supplying a constant ability to aspirate an area with or without contemporaneous irrigation.

Numerous needle type injectors, irrigators, aspirators and combinations of these devices have been utilized in the past for supplying solutions of medicinal materials and/or suction to a tissue surface once the tissue surface of interest has been mechanically exposed to the health care professional.

Quintin U.S. Pat. No. 1,189,735 of July 4, 1916 for Dental Injector and Extractor disclosed a device which applied heated air to the tip of a dental handpiece for drying purposes and had a valve to convert the air flow to suction to aspirate waste fluids, tooth debris and the like.

Hirsch U.S. Pat. No. 3,035,351 for Method of Root Canal and Periodontal Therapy, of May 22, 1962, discloses a tip for flushing root canals of teeth by feeding fluids to multiple passages in the device which extend radially from the tip. This device is not so constructed as to apply suction and would require a second device for this purpose.

Malmin U.S. Pat. No. 3,745,655, for Endodonic Irrigating Instrument, of July 17, 1973, shows a handpiece with a connection to a vacuum source, and a magazine to receive a hypodermic ampule. The handpiece includes a valve which selectively couples the vacuum source, a duct or the ampule duct to a single passage tip. In this device there is no opportunity to easily select among multiple irrigants; there is a limited volume of irrigant which is stored in the handpiece and the operation requires the manual imposition of pressure on the plunger for the ampule to dispense irrigant.

Zorzi U.S. Pat. No. 3,164,153, of Jan. 5, 1965, for Dental Apparatus, disclosed an apparatus having a reservoir for irrigant and one for aspirated waste. The device is selectively utilized as either a flushing instrument or as an aspirating instrument in accordance with a valve control on the handle. The device is cumbersome and does not allow for rapid selection between multiple irrigants.

Similarly, Kahn U.S. Pat. No. 3,871,099, of Mar. 18, 1975 for Method for Cleaning Cavities With A Combined Fluid Delivering and Aspirating Instrument, discloses a syringe-like device capable of supplying a single fluid and capable of applying suction via a simple valve and tubing system. This device does not have the ability to supply multiple irrigants easily or to apply suction simultaneously with the irrigant.

In many procedures and particularly endodonic procedures it has been necessary to have several assistants attending the patient being treated. Most of the above devices have sought to relieve the congestion of personnel around the patient by performing functions which formerly required attending assistants. In the case of these devices the assistants are removed somewhat from the treatment area, however, in most instances their services are required where multiple irrigants are utilized to either refill and supply irrigant reservoirs or to manipulate aspirating devices.

With the rapidly increasing costs of health care a device is needed that will streamline patient care and free health care professionals to see more patients in an increasingly efficient manner.

Therefore, it is an object of the present invention to provide an instrument which will provide a larger than normally available storage supply of selected medicinal fluids to minimize refilling down-time.

It is another object of the present invention to provide an instrument that can dispense, at variable pressures, one of a number of medicinal fluids, water, air and suction.

It is another object of the present invention to provide an instrument that can accommodate disposable fluid supply means to facilitate rapid interchange of relatively inexpensive prefilled medicinal fluid containers.

It is a further object of the present invention to supply multiple services from one small, light-weight handpiece which can be easily used in "one hand" type operation while freeing the professional to perform other useful functions with the free hand and freeing other assistant-type personnel to perform other tasks.

SUMMARY OF THE INVENTION

The above objectives of the invention may be typically achieved by a health services instrument for the irrigation and aspiration of a tissue surface including a plurality of medicinal fluid sources and a vacuum source. The instrument comprises a supply station having a multipart body with a fluid and vacuum supply, a means to secure the multipart body in a substantially gas tight fashion, and a locking system to hold the parts of the body in the gas tight arrangement, a means to pressurize the interior of the station, and to regulate the pressurization. The device also has means to support the fluid sources within the multipart body. The device also has a control box having selective coupling means to select among the fluid sources and to communicate with a valving means. The system also has a handpiece comprising an elongate means with a body formed with a first and second conduit for fluids and vacuum, a passage for signal communication, a nozzle, composed of a first and second concentric tip, and a first and a second finger operable control to drive the valves which are disposed between the fluid supply and the nozzle.

BRIEF DESCRIPTION OF THE DRAWINGS

FIG. 8 is a perspective view of one form of a handpiece according to the present invention;

FIG. 9 is a perspective view of a modified form of a handpiece;

FIG. 10 is a partially schematic view of a modified embodiment of a selective coupling means.

FIG. 11 is a perspective view of one form of a conduit employed between the handpiece and the supply station; and FIG. 12 is a perspective view of a modified form of a conduit.

DESCRIPTION OF THE PREFERRED EMBODIMENTS

Figure 1:
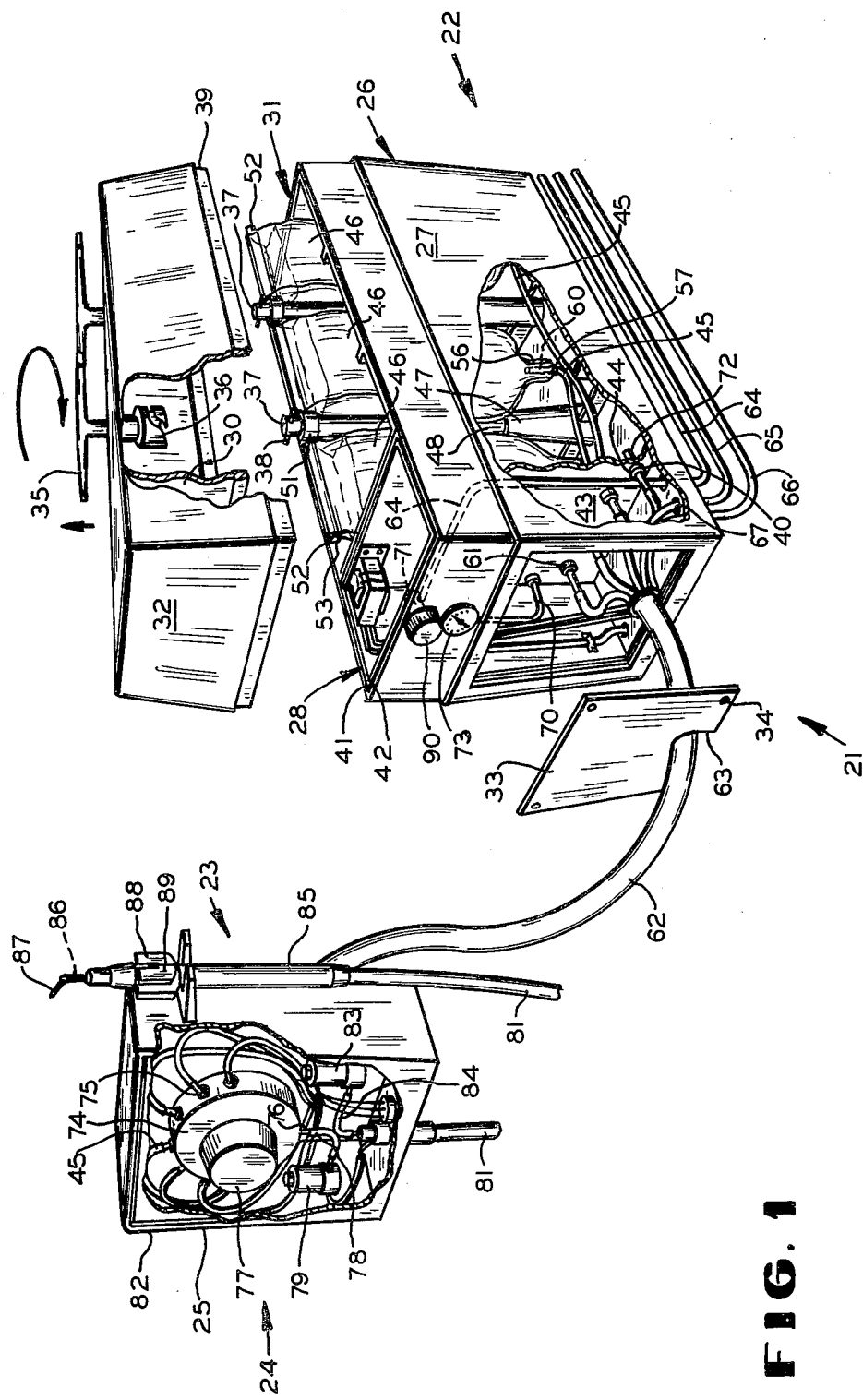
FIG. 1 is an exploded, fragmentary view of a health services system according to this invention with portions broken away to show internal elements and a show selective coupling means separated from the supply station.
Figure 2:
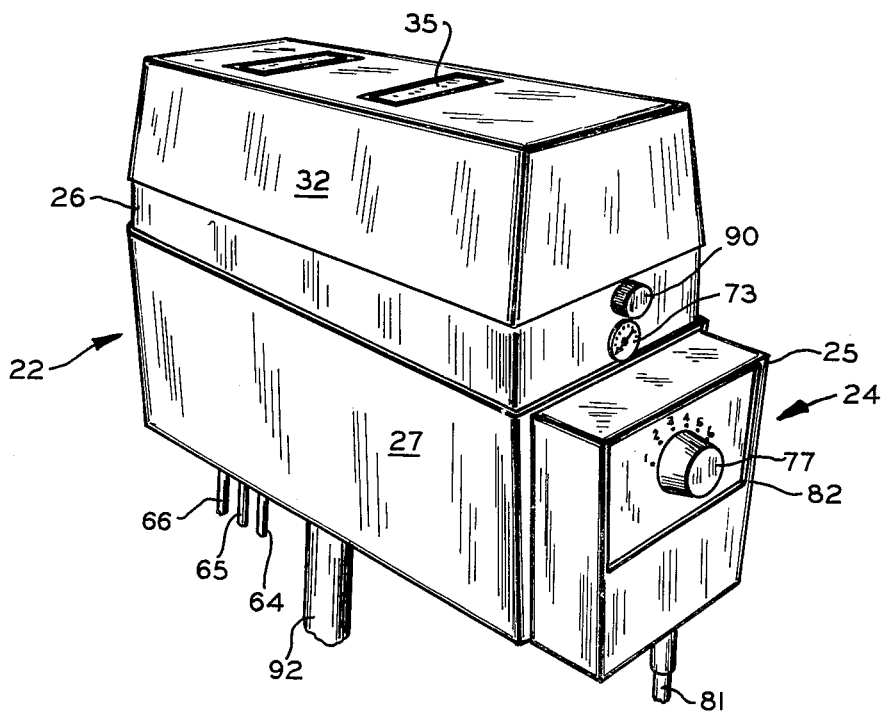
FIG. 2 is a perspective view of the health services system of FIG. 1 with a selective coupling means secured to the supply station.

A health services system for providing a health care professional with means to irrigate and aspirate a tissue surface which has been exposed mechanically for his examination and treatment is shown in FIGS. 1 and 2. The system provides means to supply multiple medicinal solutions, like saline or antiseptic, wash water and a vacuum source for suction capability to aspirate the excess solutions in the treatment area as well as tissue debris-like tooth or tissue fragments. The system provides a large supply of different medicinal solutions and suction from a remote supply station and delivers the solutions and suction via a conduit system to a small, light-weight handpiece. The handpiece is constructed so as to allow easy one-handed operation of the handpiece so the other hand can be free to hold a dental mirror, retract an organ or perform other necessary functions. Also the tapered design of one end of the handpiece allows the tip system of the handpiece to reach inaccessible areas.

Referring to the drawings wherein like reference numerals designate similar parts throughout, there is shown a health services system 21, as seen in FIG. 1, having a supply station 22, a handpiece 23 and a selective coupling means 24, shown in this embodiment as a control station 25.

As seen in FIG. 1, the supply station 22 is composed of a multi-part container 26 having a base 27, which is divided into a forward compartment 28 and a rearward compartment 31, a closure 32 at its top and a faceplate 33 secured to the forward compartment 28. The faceplate 33 is secured to the forward compartment 28 by screws 34. Closure 32 is partitioned as is base 27 by wall 30 sealably engageable with base subdividing wall 43. The closure 32 is secured to the base 27, so as to create a gas tight seal between the two parts, by a system including the locking handle 35, cam and latch mechanism 36, the upper post 37 and lock bayonet 38. This latch system operates to hold the closure 32 tightly to the base 27 to make a gas tight seal. The base 27 contacts the closure 32 by a tongue 39 and groove 41 system with a flexible gasket 42 secured into the bottom of the groove to effectuate a tight seal.

Considering the base 27, in particular the rearward compartment 31, it is seen that the two compartments are separated by a wall 43 which is fitted with apertures 44 to receive sealed fittings 40 through which fluid tubes 45 communicate. The rearward compartment, in this embodiment forms a vessel which contains and suspends fluid reservoirs 46 by a suspension system having a post sleeve 47 upstanding from the bottom of compartment 31 into which is journaled the vertical shaft 48 onto which at its upper end is engaged a shaft collar 51. Through the shaft collar 51 extend a set of support bars 52, which are passed through pockets 53 formed integral with the flexible sheet walls of the fluid reservoirs 46. At the extreme upper end of the vertical shaft 48 and above the shaft collar 51 there is the upper post 37 through which is inserted the lock bayonet 38, described previously.

Figure 3:
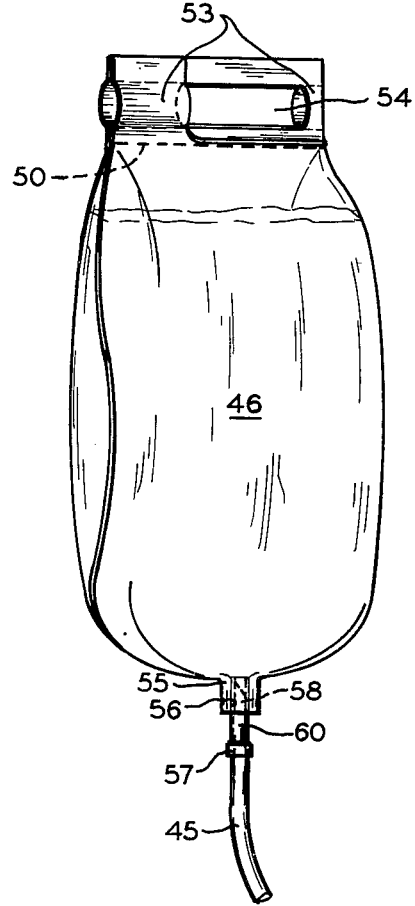
FIG. 3 is a perspective view of a disposable irrigating fluid reservoir.
Figure 4:
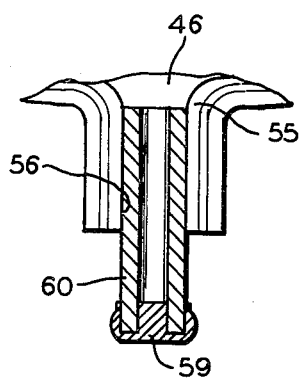
FIG. 4 is an enlarged fragment of a front elevational view of the bottom portion of the irrigating fluid reservoir of FIG. 3, in section, showing a coupling typically used in the invention.
Figure 5:
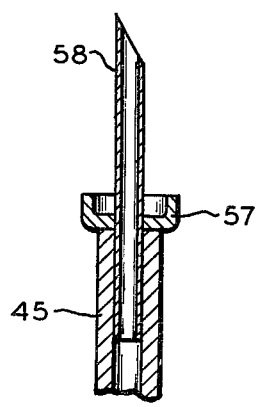
FIG. 5 is an enlarged fragment of a section of fluid conduit and a coupling to the fluid reservoir.

As seen in FIG. 1 and shown in more detail in FIGS. 3 and 4 the fluid reservoirs 46 are typically flexible walled, prefilled polyvinylchloride bags. These bags are arranged to have, at their top ends, a suspension pocket 53 which receives the support bars 52. At the bottom of the fluid reservoirs 46 there is a constriction or neck 55 having an opening forming an exit port 56 into which is inserted an exit tube 60 which is sealed with a cap 59 after the bag has been filled with the solution of choice. To sample the solution, the cap 59 is pierced by a hollow exit needle 58 which is attached to the end of a fluid tube 45. Typically, the cap 59 is heat sealed to the exit tube 60 and the exit tube 60 is heat sealed to the neck 55 to assure a no-leak seal while the exit needle 58 is usually stainless steel or acrylic in composition, and similarly sealed into place in the end of the fluid tube 45.

The fluid tubes 45 lead from the fluid sources 46 in the rearward compartment into the forward compartment via the apertures 44 in the wall 43. The apertures 44 are usually fitted with a nipple type fitting 40 or surrounded with a gasket ring 61 to provide a gas tight seal between the wall 43 and the fluid tubes 45.

In the forward compartment the fluid tubes 45 are collected into a supply conduit 62 which passes through a conduit aperture 63 in the face plate 33. The supply conduit 62 snugly fits through the conduit aperture 63 in the face plate 33. External sources of air, vacuum and water are introduced into the bottom of the forward compartment 28 by the airline 64, the vacuum line 65 and the water line 66. These lines enter through appropriately spaced apertures 67 with the vacuum and water lines also being collected into the supply conduit 62.

The air line 64 is directed to an air pressure regulator 71 and therefrom through the wall 43 into the rearward compartment 31. When the closure 32 is secured to the base 27 the air pressure in compartment 31 builds up the level preset on the pressure regulator 71 and this pressure is exerted on the walls of the fluid reservoirs 46 causing them to transmit a pressure head to the fluid in the reservoirs 46.

The air pressure within the rearward compartment 31 is bled into a second air line 72 which is collected into the supply conduit 62 as seen in FIG. 1. The pressure on the interior of the rearward compartment 31, conveyed through tube 70, is sensed by an air pressure gauge 73 to allow controlled adjustment of the pressurization.

The supply conduit 62 terminates at the selective coupling means 24, here shown as the single selector valve 74 equipped with a plurality of inlet fitting 75 and a single outlet fitting 76. Each fluid tube 45 connects to one of the inlet fittings 75. As the selector knob 77 is rotated one of the inlet fittings 75 is coupled allowing the fluid to flow to the outlet fitting 76. The outlet fitting 76 is connected by an outlet line 78 to a first valve 79, typically a solenoid controlled valve as shown here. The outlet line 78 exits the first valve 79 and leads into a second supply conduit 81 which terminates at the handpiece 23.

As seen in FIG. 1 the selector valve 74 and first solenoid valve 79 are mounted inside the control box 82. A second valve 83 is mounted on the inside of the control box 82 also. This second valve is also a solenoid controlled valve and it accepts the vacuum line 65 from supply conduit 62 and allows the vacuum supply to communicate with the vacuum output line 84 from the second supply conduit 81 and the handpiece 23.

The second supply conduit 81 terminates at a second end of the handpiece 23 to supply the handpiece 23 with fluids and vacuum. The handpiece 23 has an elongate body 85 with a first tip 86 within a second tip 87 at the first end of the handpiece 23, the first end being opposite the second end of the handpiece 23. Mounted adjacent the first end of the handpiece 23 are a first finger operable control 88 and a second finger operable control 89. The first finger operable control 88 is arranged to activate the first valve 79 which allows the pressurized fluid in one of the fluid sources 46 selected by selector valve 74 to be forced through the fluid line 78 up to the second end of the handpiece 23. At the second end of the handpiece the fluid line is coupled to a first conduit in the body of the handpiece which communicates with the first tip 86 on one end of the handpiece 23. The first valve 79 is closed until the first finger control 88 is activated at which time the valve is driven to the open position allowing fluid flow to the first tip 86.

The second finger operable control 89 drives the second valve 83 which also is in a closed state until the second control 89 is activated. When the second valve 83 is opened, the vacuum is drawn at the second tip 87.

As understood from the above description either or both control 88 or 89 may be activated at the same time. This allows for irrigation alone, aspiration alone, or simultaneous irrigation and aspiration of the area of interest.

As seen in this embodiment, the supply station 22 can be mounted out of the way with the control box 82 and handpiece 23 being the only components of the system being placed near the treatment area, minimizing the space used near the operator.

If the supply station 22 is mounted relatively far away from the treatment area the pressure within the station 22 may be adjusted by the air regulator 71 to assure the proper flow of fluids to the handpiece. Notice that the fluid reservoirs 46 are easily removed from and placed in the supply station 22 so as to minimize the time needed to recharge the system. Also, the fluid reservoirs 46 are considerably larger than previously used fluid reservoirs and may easily be mass produced and shipped to the user to eliminate the time consuming chore of solution mixing in the office or medical prep lab.

FIG. 2 shows the system 21 of FIG. 1 with the control box 82 secured to the supply station 22. In this embodiment the supply station 22 is supported by a pedestal 92 so that, if desired, the entire system 21 may be placed next to the patient treatment area. This embodiment is typically used in a dental care center as opposed to a surgical theater usage.

A typical reservoir as shown in FIG. 3 has a double walled top region pierced to form a hand hole 54 with the rod pocket 53 spanning that hand hole and thus located in the reinforced region of the flexible sheet material making up the bag like reservoir. A seal line 50 is formed below the reinforced region so that the reservoir is completely sealed and maintains its contents free of contaminants when seal 59 is unbroken. When the reservoir is coupled to the system a cup 60 coaxial of the needle 58 embraces and closely fits the pierced seal 59 to maintain the system integrity against contamination and enhance the security of the coupling.

Figure 6:
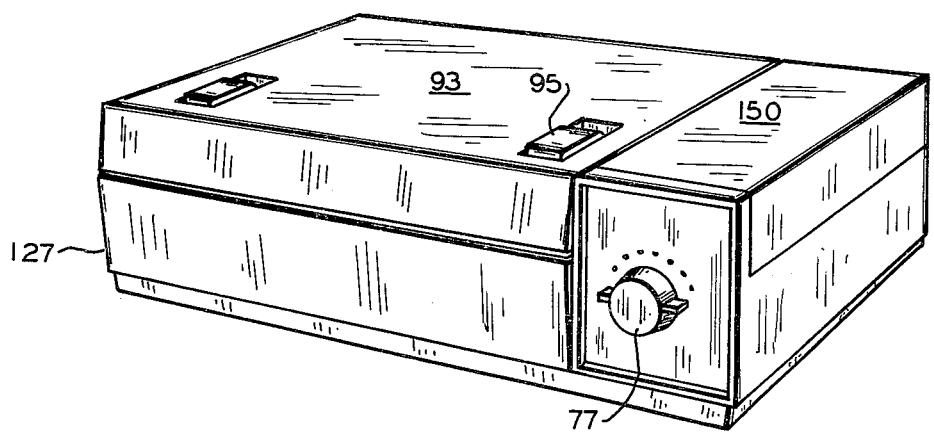
FIG. 6 is a perspective view of a modified form of the selective coupling means and supply station of the invention.
Figure 7:
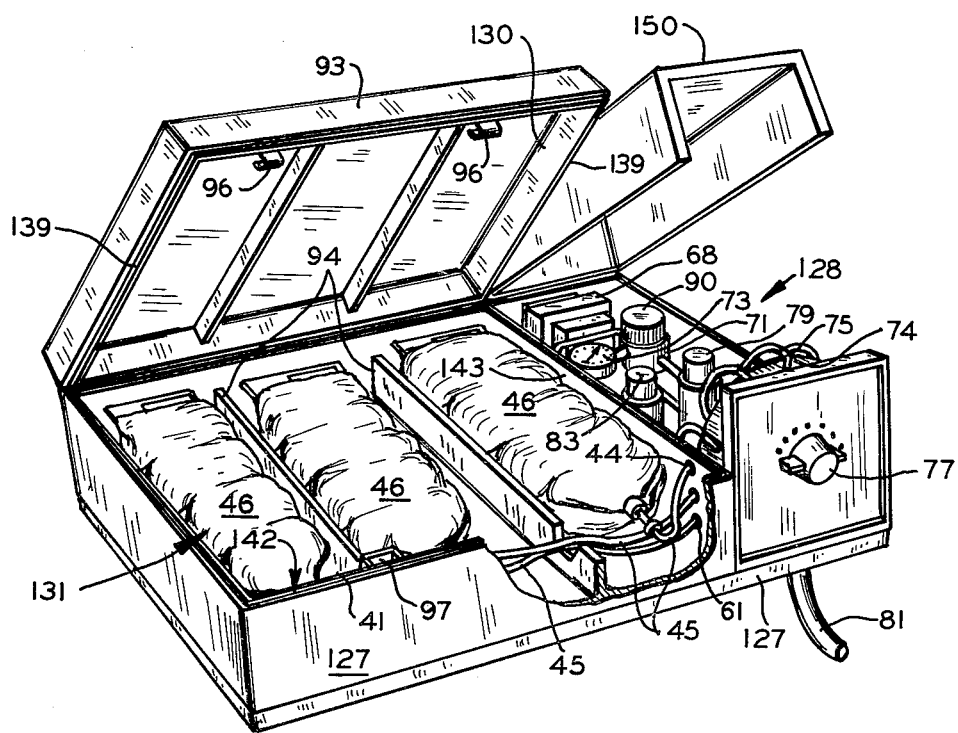
FIG. 7 is a fragmentary perspective view of a modified embodiment of the invention shown in FIG. 6.

FIGS. 6 and 7 show a perspective view of a modified form of the selective coupling means and the supply station in what is termed the desk-top model. As seen in FIG. 7 the control compartment 128 is laterally adjacent the reservoir compartment 131 in this embodiment with the two compartments still serving the same relative purposes and being separated again by the wall 143. Instead of a unitary closure 32 this embodiment employs a two part closure 93, with both parts hingedly secured to the back of the base 127.

As seen in FIG. 7 the supply station section containing the fluid sources 46 is closed in a gas tight fashion by partition 143 in base 127 cooperating with lid side 130 through the compression of gasket 142 by tongue 139.

Also, in this embodiment the fluid sources 46 rest on the floor of the pressurized compartment 131 and are maintained in their proper orientation by the divider panels 94.

In this embodiment as seen in FIG. 7, only slight interior modifications from the structure of FIGS. 1 and 2 are necessary. The air regulator 71, the air pressure guage 73 and the bell transformer 68 are placed in the control compartment 128 and the devices formerly found in the control box 82 are also incorporated into the compartment 128. A hinged lid 150 closes control compartment 128.

Also in the table top model of FIG. 7 the multipart latching system of FIG. 1 is replaced by locking handles 95 attached to the snap lock fasteners 96 which cooperate with the locking loops 97 to produce the gas tight seal between the compartment closure 93 and the base 127.

FIG. 8 shows a perspective of one embodiment of the handpiece showing the handpiece 23 having the elongate body having a handgrip section 98, a first tip 86 at one end and a second tip 87 encompassing the first tip 86. Mounted adjacent said one end of the handpiece 23 are two finger operable control switches, a first finger operable switch 88 and a second finger operable finger switch 89. The handpiece 23 is supplied fluids and vacuum through the second supply conduit 81.

As seen in FIG. 8, the first tip 86 is typically a small bore needle of such a material that it can allow passage of many types of fluids without corrosion of the needle. The second tip 87 is typically plastic and tapered toward its end so it may gain access to tight areas and thereby lend great versitility to the device. The second tip 87 surrounds the first tip 86 and is spaced radially apart therefrom at such a distance as to allow the aspiration of small tissue and tooth fragments. Both tips are adapted for convenient replacement (by means not shown).

It is within the contemplation of this invention to employ various control means for the release of fluids (both liquid and gaseous) from tip 86 and the withdrawal of fluids and debris by means of tip 87. For example a switch having an activator which slides longitudinally of the barrel 98 can be arranged to have positions opening all control circuits, closing a circuit to open fluid control valve 79 and issue fluid through tip 86, closing a circuit to open vacuum control valve 83, and closing both the circuits to valves 79 and 83. Thus alternatives to switches 88 and 89 for digital control of the valves for no flow, flow in the fluid issuing or fluid withdrawing lines or both lines are available at the handpiece. Further, the selection of issued fluids from the tip 86 can be controlled by means at the handpiece.

While valves for controlling the flow of each of the fluids from tip 86 could be provided in the handpiece with supply lines from the reservoirs 46 to the handpiece extending within the sheath of conduit 81, a preferred arrangement where fluid selection is afforded at the handpiece is to incorporate a selector switch in the handpiece and selectively responsive valved paths in a select control remote from the handpiece. This permits a single fluid supply conduit to be utilized in the conduit sheath between the handpiece and the selector control. For example, the rotary selector valve 74 can be provided with a pulse activated solenoid driven stepping mechanism (not shown) such that the activation of a selector switch (not shown) on the handpiece advances the valve in a step-by-step manner to valve the desired fluid on a one step per pulse basis. In a first position of the selector valve 74, as determined by one pulse from a neutral or home position, the valve can couple the tap water input 66 to the output fitting 76. A second position of valve 74, established by two pulses from the handpiece switch, can couple a saline solution reservoir 46 to output fitting 76. A third position of valve 74 for another irrigant can be established by three pulses from the handpiece switch.

FIG. 9 shows a perspective view of a modified form of the handpiece 23 showing a selector switch 99 on the handpiece which drives a fluid selector means (not shown) which selects one of the plurality of fluid conduits coupled to reservoirs 46.

FIG. 10 shows a modified form of the selective coupling means wherein the selector 99 drives an array of solenoid controlled valves 102. In the embodiment each one of a plurality of fluid sources 46 is connected to one of the valves in the array by a connector tube 103. The outputs of the valves are then connected to the handpiece 98 by individual tubes 100 in the unitary supply conduit 104 which connects to the second end of the handpiece 98 to supply fluids.

In this embodiment each of the valves of the array 102 is in a closed state until selected on the selector switch 99 at which time the valve is opened to allow fluid flow to the handpiece 23. As the selector is rotated to a new selection the activation signal is discontinued and the valve relaxes to its off state automatically.

FIG. 11 is a perspective view of the second supply conduit 81 typically used in the invention. The conduit has a flexible hollow body 105 which encases an interior fluid tube 106 which carries the fluid selected and interior electrical signal line tube 107. The hollow center 108 typically is used as the large diameter vacuum line. Conductors 109 from switches 88 and 89 and/or 99 extend within tube 107 to controls such as solenoides 79, 83 and 102.

In an alternative embodiment, as seen in FIG. 11, the hollow center 111 and conductor tube 112 remain but the single interior fluid tube is replaced by a plurality of smaller diameter fluid tubes 113. These tubes allow for the transportation of each separate fluid to the handpiece 23 without them passing through the length of the supply conduits one after another. This configuration is significant when the solutions react with each other and may damage the conduit by so doing.

Variations in the arrangement of elements of the instrument of this invention can be made to suit the needs of the utilization for which it is intended. For example, where the control unit 82 is remoted from the supply station 22, the pressure regulator control knob 90 shown on the end of supply station 22 in FIG. 1 can be located in control unit 82 with the gas pressure line 64 extending to the control unit and the regulator valve 71 therein. Pressure regulated gas is conveyed to the supply station reservoir chamber 31 through the sheath of conduit 62 in this instance.

Other forms of control signals than those illustrated can be employed. Pneumatic or hydraulic signalling means and control elements responsive to their signals can be utilized, particularly in explosive atmosphere conditions of some anesthetics. Electrical signals can be multiplexed and digital coded signals can also be used for both fluid selection and the flow control.

In accordance with the provisions of the patent statue the principles and mode of operation of the present invention has been illustrated and described in what is now considered the best embodiments of the invention. However, it is understood that the invention may be practiced otherwise than as specifically illustrated and described without departing from its spirit or scope.

What is claimed is:

1. A system for irrigating and aspirating a tooth cavity comprising an elongate handpiece having first and second ends; a first tip on said first end of said handpiece; a second tip on said first end of said handpiece coaxial with adjacent to, encompassing, and spaced radially from said first tip; a first finger operable control on said handpiece adjacent said first end of said handpiece for causing fluid to issue from said first tip; a second finger operable control on said handpiece adjacent said first end of said handpiece and contiguous to said first finger operated control for causing a vacuum to be drawn at said second tip, whereby said first and second finger operated controls are selectively and simultaneously operable with a single finger; a first conduit for fluid extending from said second end of said handpiece opposite said first end and in communication with said first tip; a second conduit for drawing a vacuum extending from said second end of said handpiece and in communication with said second tip; a vacuum source remote from said handpiece; second valve means remote from said handpiece and responsive to said second control for connecting said vacuum source to said second conduit; a plurality of irrigating fluid sources remote from said handpiece; means for imposing a head on said irrigating fluid sources; means remote from said handpiece for selectively coupling each of individual ones of said plurality of said irrigating fluid sources to said first conduit; and first valve means in said first conduit between said first tip and said means for selective coupling and remote from said handpiece, responsive to said first control for controlling the flow of fluids between said selective coupling means and said handpiece.

2. Apparatus according to claim 1 wherein said first finger operable control comprises an electric switch and said first valve is a solenoid controlled valve.

3. Apparatus according to claim 1 wherein said second valve comprises a solenoid operated valve and said second finger operated control comprises an electric switch.

4. Apparatus according to claim 1 wherein said selective coupling means comprises a single selector valve having a plurality of inlet ports and a single outlet port and being disposed between said fluid sources and said first conduit.

5. A system for irrigating and aspirating a tooth cavity comprising an elongate handpiece having first and second ends; a first tip on said first end of said handpiece; a second tip on said first end of said handpiece coaxial with, adjacent to, encompassing, and spaced radially from said first tip; a first finger operable control on said handpiece adjacent said first end of said handpiece for causing fluid to issue from said first tip; a second finger operable control on said handpiece adjacent said first end of said handpiece and contiguous to said first finger operated control for causing a vacuum to be drawn at said second tip, whereby said first and second finger operated controls are selectively and simultaneously operable with a single finger; a first conduit for fluid extending from said second end of said handpiece opposite said first end and in communication with said first tip; a second conduit for drawing a vacuum extending from said second end of said handpiece and in communication with said second tip; a vacuum source remote from said handpiece; second valve means remote from said handpiece and responsive to said second control for connecting said vacuum source to said second conduit; a plurality of irrigating fluid sources remote from said handpiece; means for imposing a head on said irrigating fluid sources; a selector on said handpiece for issuing a plurality of distinct signals; means remote from said handpiece responsive to respective distinct signals from said selector for selectively coupling each of individual ones of said plurality of said irrigating fluid sources to said first conduit; and first valve means in said first conduit between said first tip and said means for selectively coupling and remote from said handpiece, responsive to said first control for controlling the flow of fluid between said selective coupling means and said handpiece.

6. Apparatus according to claim 5 wherein said selector is an electric selector switch and said remote means is a single valve having a plurality of inputs a single output and a coupling path selectively connectible between individual inputs and said output and means to couple said respective valve inputs with respective ones of said plurality of irrigating fluid sources.

7. Apparatus according to claim 5 wherein said selector is an electric selector switch and said remote means is an array of solenoid controlled valves each of which is disposed between a single fluid source and said first conduit and each of said valve solenoids being responsive to said electric selector switch.

* * * * *